(12) United States Patent
Baumann et al.

(10) Patent No.: US 10,299,747 B2
(45) Date of Patent: May 28, 2019

(54) DEVICE HAVING A C-ARM AND X-RAY IMAGER

(71) Applicants: Berthold Baumann, Kastl (DE); Ralf Gärtner, Kemnath (DE); Michael Kleber, Eslarn (DE); Thomas Kleber, Moosbach (DE); Alexander Krämer, Irchenrieth (DE); Harald Mulzer, Speinshart (DE); Wolfgang Neuber, Pressath (DE); Matthias Schirbl, Freihung (DE); Josef Zeidler, Marktredwitz (DE)

(72) Inventors: Berthold Baumann, Kastl (DE); Ralf Gärtner, Kemnath (DE); Michael Kleber, Eslarn (DE); Thomas Kleber, Moosbach (DE); Alexander Krämer, Irchenrieth (DE); Harald Mulzer, Speinshart (DE); Wolfgang Neuber, Pressath (DE); Matthias Schirbl, Freihung (DE); Josef Zeidler, Marktredwitz (DE)

(73) Assignee: Siemens Healthcare GmbH, Erlangen (DE)

( * ) Notice: Subject to any disclaimer, the term of this patent is extended or adjusted under 35 U.S.C. 154(b) by 203 days.

(21) Appl. No.: 15/404,280

(22) Filed: Jan. 12, 2017

(65) Prior Publication Data
US 2017/0202529 A1   Jul. 20, 2017

(30) Foreign Application Priority Data
Jan. 15, 2016  (DE) .................... 10 2016 200 442

(51) Int. Cl.
*A61B 6/00* (2006.01)

(52) U.S. Cl.
CPC .......... *A61B 6/4441* (2013.01); *A61B 6/4476* (2013.01)

(58) Field of Classification Search
CPC .................................................. A61B 6/4441
See application file for complete search history.

(56) References Cited

U.S. PATENT DOCUMENTS

| 7,543,986 B2 | 6/2009 | Saffer |
| 2007/0280426 A1 | 12/2007 | Saffer |

FOREIGN PATENT DOCUMENTS

| DE | 102004011460 A1 | 10/2005 |
| DE | 102010021657 A1 | 12/2011 |

OTHER PUBLICATIONS

German Office Action for related German Application No. 10 2016 200 442.5 dated Sep. 15, 2016, with English translation.

*Primary Examiner* — Dani Fox
(74) *Attorney, Agent, or Firm* — Lempia Summerfield Katz LLC

(57) ABSTRACT

The disclosure provides a device having a C-arm, the C-arm including a main body of which the cross-sectional profile is formed as a double H, an outer wall, an inner wall and two side walls of the main body forming a rectangular cavity. The device also includes running wires arranged on the main body and running rollers, on which the C-arm is movably mounted, rolling on the running wires. The running wires and the running rollers are arranged in such a way that at least 50 percent of the mounting forces acting on the running wires due to the running rollers is introduced into the side walls of the main body. The disclosure also provides an x-ray imager having such a device. The disclosure offers the advantage that undesired oscillations of the C-arm are avoided.

15 Claims, 4 Drawing Sheets

DEVICE HAVING A C-ARM AND X-RAY IMAGER

The application claims the benefit of German Patent Application No. DE 10 2016 200 442.5, filed Jan. 15, 2016, which is hereby incorporated by reference in its entirety.

TECHNICAL FIELD

The disclosure relates to a device having a C-arm, the C-arm including a main body of which the cross-sectional profile is formed as a double H. An outer wall, an inner wall, and two side walls of the main body form a rectangular cavity. Running wires are arranged on the main body and running rollers on which the C-arm is movably mounted may roll on the running wires. The disclosure also provides an x-ray imager having such a device.

BACKGROUND

C-arm machines are widely used, for example, in medical technology. In the case of such machines, a diagnostic or treatment device is fastened to a C-shaped main body. Because its shape, the C-arm, and with it the diagnostic or treatment device, may be moved orbitally around a point on a patient that is to be examined or treated. Thus, various angular positions between the patient and the diagnostic or treatment device may be achieved without the patient having to be repositioned.

Especially popular as diagnostic devices are x-ray imaging devices, in which an x-ray source is attached to one end of the C-arm and an x-ray detector or image intensifier is attached to the opposite end. The C-arm is mounted on rollers and on these may be pivoted about an orbital axis. Such a C-arm x-ray machine is described by way of example in DE 10 2004 011 460 A1.

FIG. 1 depicts part of a C-arm 1 of an x-ray imaging device according to the prior art. The C-arm 1 includes extruded aluminum. As may be seen from the drawing, the main body 2 of the C-arm 1 is formed as one piece and has in cross section the shape of a double H. The running rollers 7, which are mounted on running wires 8 made of steel that are arranged in grooves of the "ears" of the main body 2, may likewise be seen. On the running rollers 7, the C-arm 1 may perform an orbital movement about an isocenter.

Due to the position of the running wires 8, with large C-arms 8 and/or with heavy loads on the C-arm 1 the "ears" of the double-H profile may flex. This results in a relatively great, undesired displacement of the imaging components that are fastened to the C-arm. Furthermore, the decay time for the resultant oscillation in braking and accelerating operations is increased by the mutual excitement of the "ears". However, for applications such as "Needle Guidance" or 3D image recording, it is important that there is as little displacement as possible. It is likewise important for 3D image recording to have a decay time that is as small as possible, since this influences the waiting time in the end positions during the application, and consequently the overall application time.

One possible way of preventing this is not to use "ears" and to allow the running rollers to run directly on the corners of the rectangular profile. Such an arrangement is disclosed in German patent application DE 10 2010 021 657 A1.

SUMMARY AND DESCRIPTION

The scope of the present disclosure is defined solely by the appended claims and is not affected to any degree by the statements within this summary. The present embodiments may obviate one or more of the drawbacks or limitations in the related art.

The object of the disclosure is to provide a device having a C-arm and an x-ray imager that avoid the aforementioned disadvantages and make an improved C-arm movement possible.

According to the disclosure, the running wires are not fastened to the "ears" of the main body of a C-arm, but at least partially to the stable rectangular core profile of the main body. As a result, the mounting forces acting on the running wires due to running rollers are partly introduced directly into the core profile. For this purpose, the running rollers assume a slanting position in relation to one another and, as depicted in FIG. 2, are arranged in an elliptical "O".

The disclosure describes a device having a C-arm, the C-arm including a main body of which the cross-sectional profile is formed as a double H, an outer wall, an inner wall, and two side walls of the main body forming a rectangular cavity. The device also includes running wires arranged on the main body and running rollers, on which the C-arm is movably mounted, rolling on the running wires. The running wires and the running rollers are arranged in such a way that at least 50 percent of the mounting forces acting on the running wires due to the running rollers is introduced into the side walls of the main body. This takes place because the outer wall and the inner wall are extended beyond the rectangular cavity and form on each side of the main body two projecting legs. Each leg forms with a side wall an edge or a corner running along the main body. The running wires are arranged in or on running wire carriers arranged along the edges or corners.

The disclosure offers the advantage that an O arrangement of the running rollers and a direct introduction of forces at the core profile of the C-arm have the effect of producing a smaller spatial deviation of an x-ray source fastened to the C-arm in relation to the x-ray detector. Furthermore, the decay time for resultant oscillations in braking and accelerating operations of the C-arm in the end positions is reduced. The amplitudes of the resultant oscillations in braking and accelerating operations in the end positions are also reduced.

In a further embodiment, the running rollers may be arranged in such a way that the axes of rotation of the running rollers rolling on various running wires of each side of the main body have in relation to one another an axis angle greater than 20 degrees, such as an axis angle of 45 degrees.

In an embodiment of the device, the running wire carriers may be formed in one piece with the main body.

In an embodiment, the surfaces of the running wire carriers that are facing the running rollers form with the associated side wall an angle of inclination of 45 degrees.

In a further embodiment, the main body may be made of aluminum and the running wires may be made of steel.

The disclosure also provides an x-ray imager having the device described herein, wherein an x-ray source is arranged at one end of the C-arm and x-ray detector is arranged at the other end of the C-arm.

BRIEF DESCRIPTION OF THE DRAWINGS

Further details and advantages of the disclosure may be seen from the explanations that follow of an exemplary embodiment based on schematic drawings, in which.

DETAILED DESCRIPTION

Figure 1:
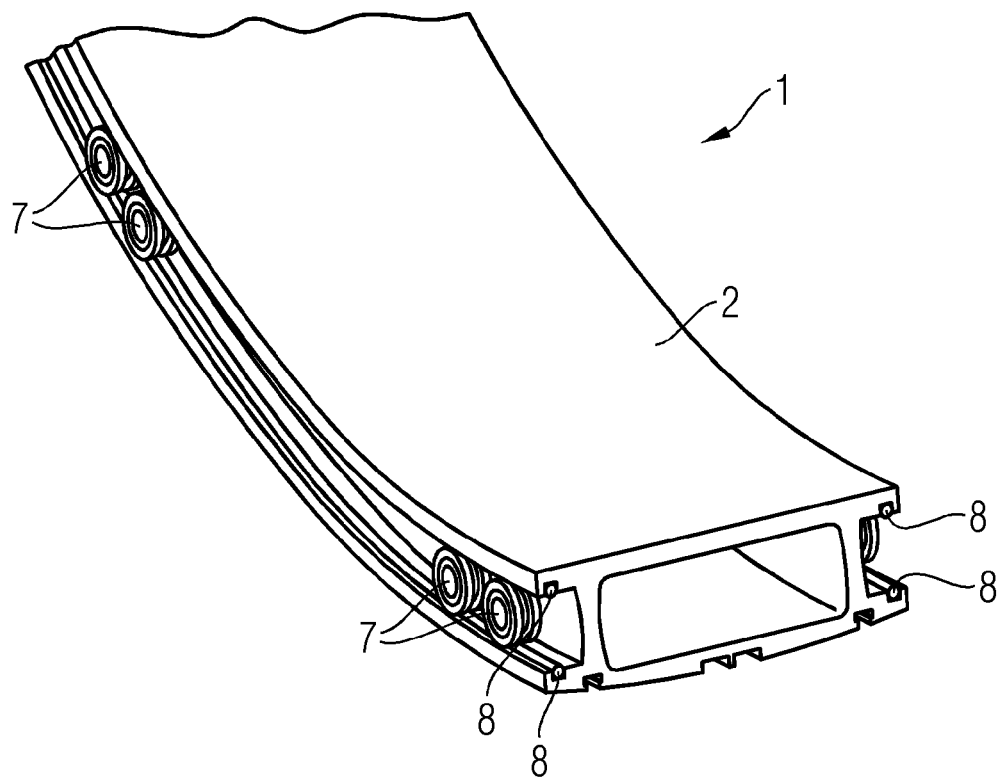
FIG. 1 depicts a spatial view of part of a C-arm according to the prior art.
Figure 2:
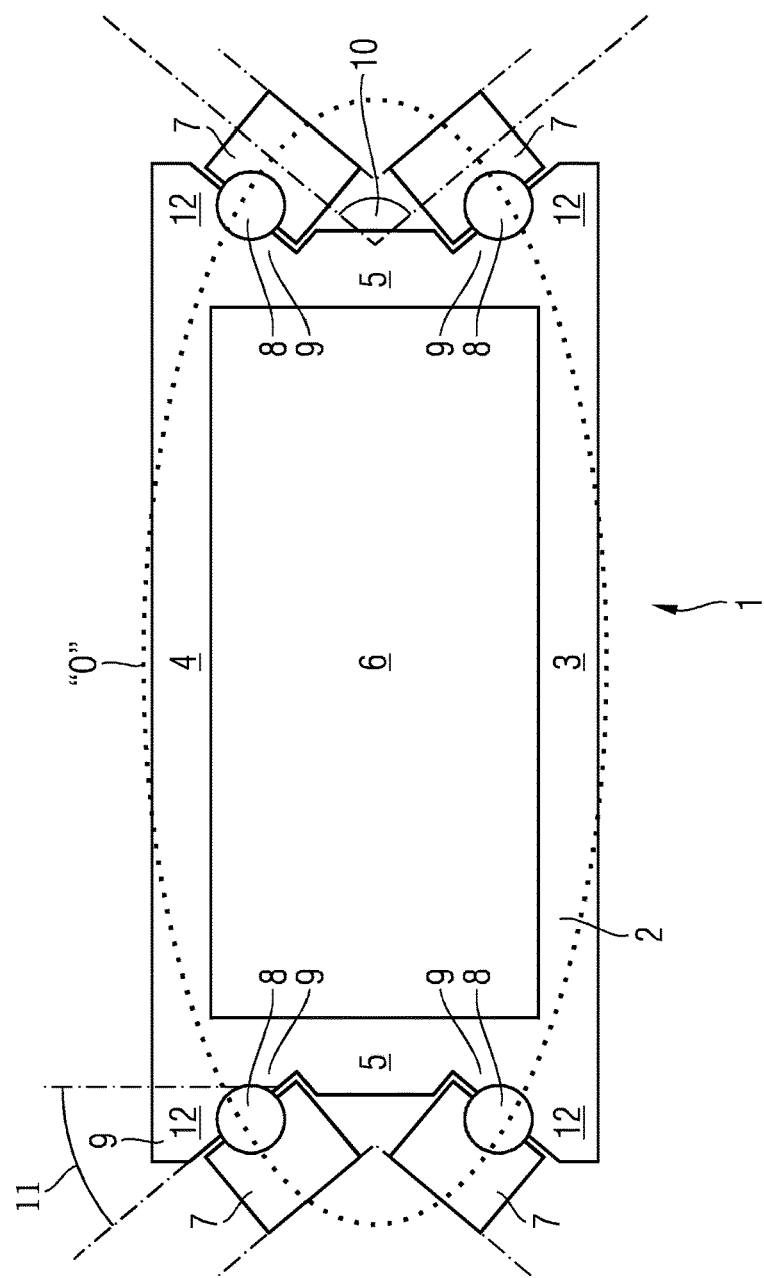
FIG. 2 depicts an example of a cross section through a C-arm.

FIG. 2 depicts a cross section through a C-arm 1, which is movably mounted on running rollers 7. The C-arm 1 includes a main body 2, which in cross-sectional profile, forms a double H. In the core region (e.g., between the outer wall 3, the inner wall 4, and the side walls 5), the main body 2 forms a rectangular cavity 6. The outer wall 3 and the inner wall 4 of the main body 2 are extended beyond the cavity 6 and form legs 12, known as "ears."

The legs 12 form with the side walls 5 edges or corners, in which the running wires 8 are arranged. The running rollers 7 roll on the running wires 8. The running wires 8 are set in grooves in the surface of the running wire carriers 9. The surface of the running wire carriers 9 forms with the side walls 5 an angle of inclination 11 of 45 degrees. Since the running rollers 7 are likewise inclined with respect to the side walls 5 by 45 degrees, approximately 50% of the mounting forces that are introduced into the main body due to the running rollers 7 is introduced into the side walls 5, and not 100% into the legs 12. The axes of rotation of the running rollers 7 of one side form in relation to one another an axis angle 10 of 45 degrees. In the case of this arrangement of the running rollers 7 and the running wires 8, an O-shaped arrangement of the running rollers 7 is produced, as represented by the dashed line.

The O-shaped arrangement of the running rollers 7 has the effect that the introduction of forces into the main body 2 no longer takes place at the legs 12 but directly at the stable core profile (e.g., side walls 5). An undesired deformation due to the flexing of the legs 12 is consequently avoided. Likewise, the decay time for resultant oscillations in end positions in braking and accelerating operations is reduced, since the legs 12 may no longer rock in relation to one another.

The running wire carriers 9 may be produced in one piece with the main body 2 from aluminum. The running wires 8 may be made of steel.

Figure 3:
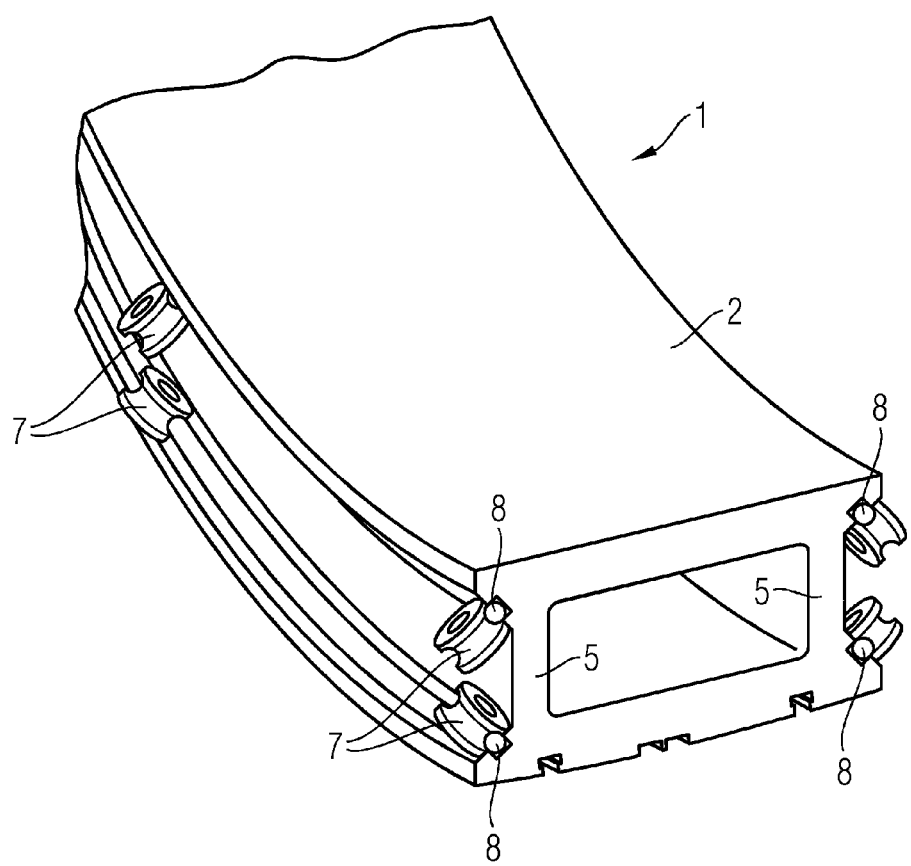
FIG. 3 depicts an example of a spatial view of part of a C-arm.

FIG. 3 depicts part of a C-arm 1 having a cross section according to FIG. 2. The running rollers 7 are inclined at 45 degrees in relation to the side walls 5 of the main body 2 of the C-arm 1. The running wires 8 are arranged in the corners or edges that are formed by the side walls 5 and the legs 12 of the main body 2. As a result, the forces caused by the running rollers 7 do not act perpendicularly on the legs 12 but partially in the direction of the side walls 5. The axes of rotation of adjacent running rollers 7 of one side of the main body 2 form in relation to one another an axis angle of 45 degrees.

Figure 4:
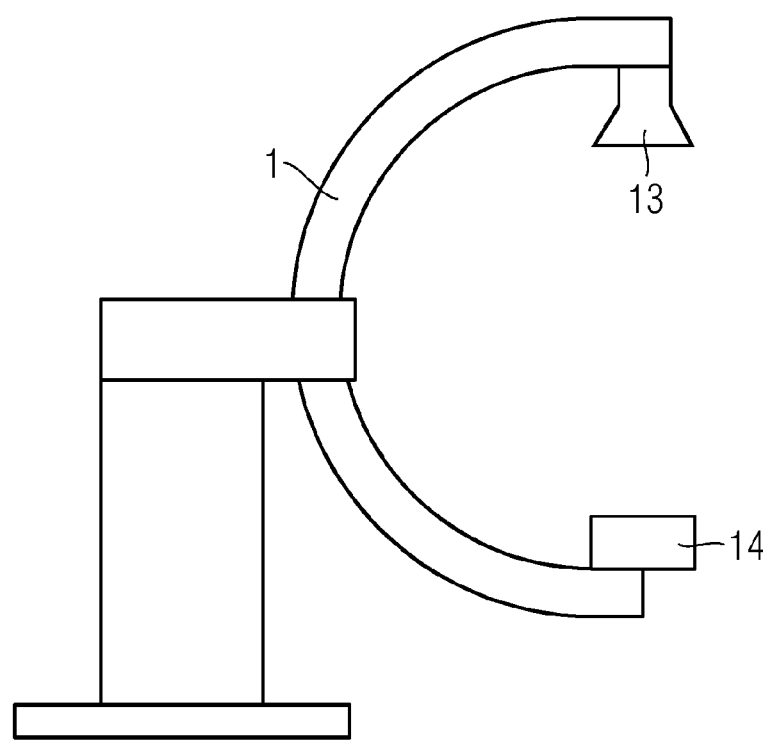
FIG. 4 depicts an example of an x-ray imager having a C-arm.

FIG. 4 depicts a side view of an x-ray imager having a C-arm 1, which is formed in a way corresponding to FIG. 2 and FIG. 3. An x-ray source 13 and an x-ray detector 14 are arranged opposite one another at the two ends of the C-arm 1.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

Although the disclosure has been more specifically illustrated and described in detail by the exemplary embodiments, the disclosure is not restricted by the disclosed examples and other variations may be derived therefrom by a person skilled in the art without departing from the scope of protection of the disclosure.

The invention claimed is:

1. A device comprising:
   a C-arm comprising a main body having a cross-sectional profile with a double H-shape, an outer wall, an inner wall, and two side walls of the main body providing a rectangular cavity;
   running wires arranged on the main body of the C-arm;
   running wire carriers, wherein the running wires are arranged in or on the running wire carriers; and
   running rollers, on which the C-arm is movably mounted, configured to roll on the running wires,
   wherein the outer wall and the inner wall are extended beyond the rectangular cavity and provide on each side of the main body two projecting legs, wherein each leg forms, with a respective side wall of the two side walls, an edge running in a longitudinal direction of the main body, and
   wherein the running wire carriers are arranged along the edges formed by each leg and the side walls and are positioned such that at least 50 percent of mounting forces acting on the running wires due to the running rollers is introduced into the two side walls of the main body.

2. The device of claim 1, wherein the running rollers are arranged such that axes of rotation of the running rollers rolling on the respective running wires on each side of the main body provide, in relation to one another, an axis angle greater than 20 degrees.

3. The device of claim 2, wherein the axis angle is 45 degrees.

4. The device of claim 3, wherein the running wire carriers are one piece with the main body.

5. The device of claim 4, wherein surfaces of the running wire carriers facing the running rollers form with a facing side wall of the main body an angle of inclination of 45 degrees.

6. The device of claim 5, wherein the main body is aluminum and the running wires are steel.

7. The device of claim 1, wherein the running wire carriers are one piece with the main body.

8. The device of claim 1, wherein surfaces of the running wire carriers facing the running rollers form with a facing side wall of the main body an angle of inclination of 45 degrees.

9. The device of claim 1, wherein the main body is aluminum and the running wires are steel.

10. An x-ray imager comprising:
    a C-arm comprising a main body having a cross-sectional profile with a double H-shape, an outer wall, an inner wall, and two side walls of the main body providing a rectangular cavity;
    running wires arranged on the main body of the C-arm;
    running wire carriers, wherein the running wires are arranged in or on the running wire carriers;
    running rollers, on which the C-arm is movably mounted, configured to roll on the running wires;
    an x-ray source arranged at a first end of the C-arm; and an x-ray detector arranged at a second, opposite end of the C-arm, wherein the outer wall and the inner wall extend beyond the rectangular cavity and forming on each side of the main body two projecting legs and each leg forming with a side wall of the two side walls an edge running in a longitudinal direction of the main body, and wherein the running wire carriers are arranged along the edges formed by each leg and the side walls and are positioned such that at least 50 percent of mounting forces acting on the running wires due to the running rollers is introduced into the side walls of the main body.

11. The X-ray imager of claim 10, wherein the running rollers are arranged such that axes of rotation of the running rollers rolling on the respective running wires on each side of the main body provide, in relation to one another, an axis angle greater than 20 degrees.

12. The X-ray imager of claim 11, wherein the axis angle is 45 degrees.

13. The X-ray imager of claim 10, wherein the running wire carriers are one piece with the main body.

14. The X-ray imager of claim 10, wherein surfaces of the running wire carriers facing the running rollers form with a facing side wall of the main body an angle of inclination of 45 degrees.

15. The X-ray imager of claim 10, wherein the main body is aluminum and the running wires are steel.

* * * * *